United States Patent [19]

Hoehn et al.

[11] Patent Number: 5,239,064
[45] Date of Patent: Aug. 24, 1993

[54] A59770 ANTIBIOTICS

[75] Inventors: Marvin M. Hoehn; Karl H. Michel, both of Indianapolis; Raymond C. Yao, Carmel, all of Ind.

[73] Assignee: Eli Lilly and Company, Indianapolis, Ind.

[21] Appl. No.: 507,551

[22] Filed: Apr. 11, 1990

Related U.S. Application Data

[63] Continuation-in-part of Ser. No. 350,866, May 12, 1989, abandoned.

[51] Int. Cl.⁵ .................. C07H 17/08; C07D 313/00; A61K 35/00
[52] U.S. Cl. ..................................... 536/6.5; 549/264; 549/268; 424/118; 424/122; 435/76; 435/872
[58] Field of Search ................. 539/264, 268; 514/450, 514/31; 536/6.5; 424/122; 435/76, 872; 519/468

[56]  References Cited

U.S. PATENT DOCUMENTS

| 3,907,832 | 9/1975 | Hamill | 549/343 |
|---|---|---|---|
| 4,766,112 | 8/1988 | Goegelman et al. | 514/30 |
| 4,874,749 | 10/1989 | Mrozik | 514/30 |
| 4,920,215 | 4/1990 | Holdom et al. | 536/16.8 |

OTHER PUBLICATIONS

T. Kihara and K. Isono, *The Journal of Antibiotics*, Sep., 1983, p. 1236.
S. Omura, H. B. Woodruff et al., *The Journal of Antibiotics*, Dec., 1988, pp. 1910-1912.
Lechevalier et al., *Int. J. Systemic Bacteriol.* 36 (1), 29-37 (1986).
A. Hirota et al., *Agric. Biol. Chem.* 53 (10), 2831-2833 (1989).
S. Omura in *Macrolide Antibiotics*, S. Omura, Ed., Academic Press, New York, 1984, pp. 509, 520-521.
H. Seto et al.; *Chem. Abstr. 112*: 94883w (1990).
Nippon Kayaku, Derwent Abstract C90-103936 of EP-381-124-A.
Kihara et al, The Journal of Antibiotics, Sep. 1983, p. 1236.
Woodruff, The Journal of Antibiotics, Dec. 1988, pp. 1910-1912.

*Primary Examiner*—Johnnie R. Brown
*Assistant Examiner*—Elli Peselev
*Attorney, Agent, or Firm*—Nancy J. Harrison; Leroy Whitaker

[57]  ABSTRACT

A novel antibiotic complex, A59770, individual factors and derivatives thereof, are provided. The A59770 compounds are useful as pesticides, particularly as rodenticides. Further provided are methods for reducing a rodent population, rodenticidal compositions, and an A59770-producing *Amycolatopsis orientalis* culture.

5 Claims, 6 Drawing Sheets

A59770 ANTIBIOTICS

CROSS REFERENCE TO RELATED APPLICATION

This application is a continuation in part of copending application Ser. No. 07/350,866, which was filed on May 12, 1989, now abandoned.

SUMMARY OF THE INVENTION

This invention relates to the antibiotic A59770 complex comprising several factors including individual factors A, B, C, D, E and F. The antibiotic A59770 complex is produced by fermentation of a strain selected from *Amycolatopsis orientalis* NRRL 18387 or an A59770-producing mutant thereof.

The A59770 antibiotics are useful as pesticidal agents, more specifically as rodenticides.

The invention also relates to a biologically-purified culture selected from *Amycolatopsis orientalis* NRRL 18387 or an A59770-producing mutant thereof.

DESCRIPTION OF THE DRAWINGS

Infrared absorption spectra (KBr disk) of A59770 factors A, B, C and D and the aglycone and pentaacetyl derivative of factor A are presented in the drawings as follows.

DETAILED DESCRIPTION OF THE INVENTION

This invention relates to antibiotic compounds; in particular, this invention relates to an antibiotic complex designated as the A59770 complex which comprises several factors, including individual factors A, B, C, D, E and F, to the individual factors and to certain derivatives of factor A. The antibiotic complex is produced by culturing a microorganism selected from *Amycolatopsis orientalis* NRRL 18387 or an A59770-producing mutant thereof. The structure of A59770A is described infra. The structures of the other antibiotic factors have not, as yet, been fully determined, but they are believed to be structurally related to factor A.

This invention also relates to a biologically-purified culture selected from *Amycolatopsis orientalis* NRRL 18387 or an A59770-producing mutant thereof.

The term "antibiotic complex", as used herein, refers to a mixture of coproduced individual antibiotic factors. As will be appreciated by those skilled in the art of antibiotic production by fermentation, the number and ratio of the individual factors produced in an antibiotic complex may vary, depending on the fermentation conditions.

Description of Individual Factors

A59770A

Figure 1:
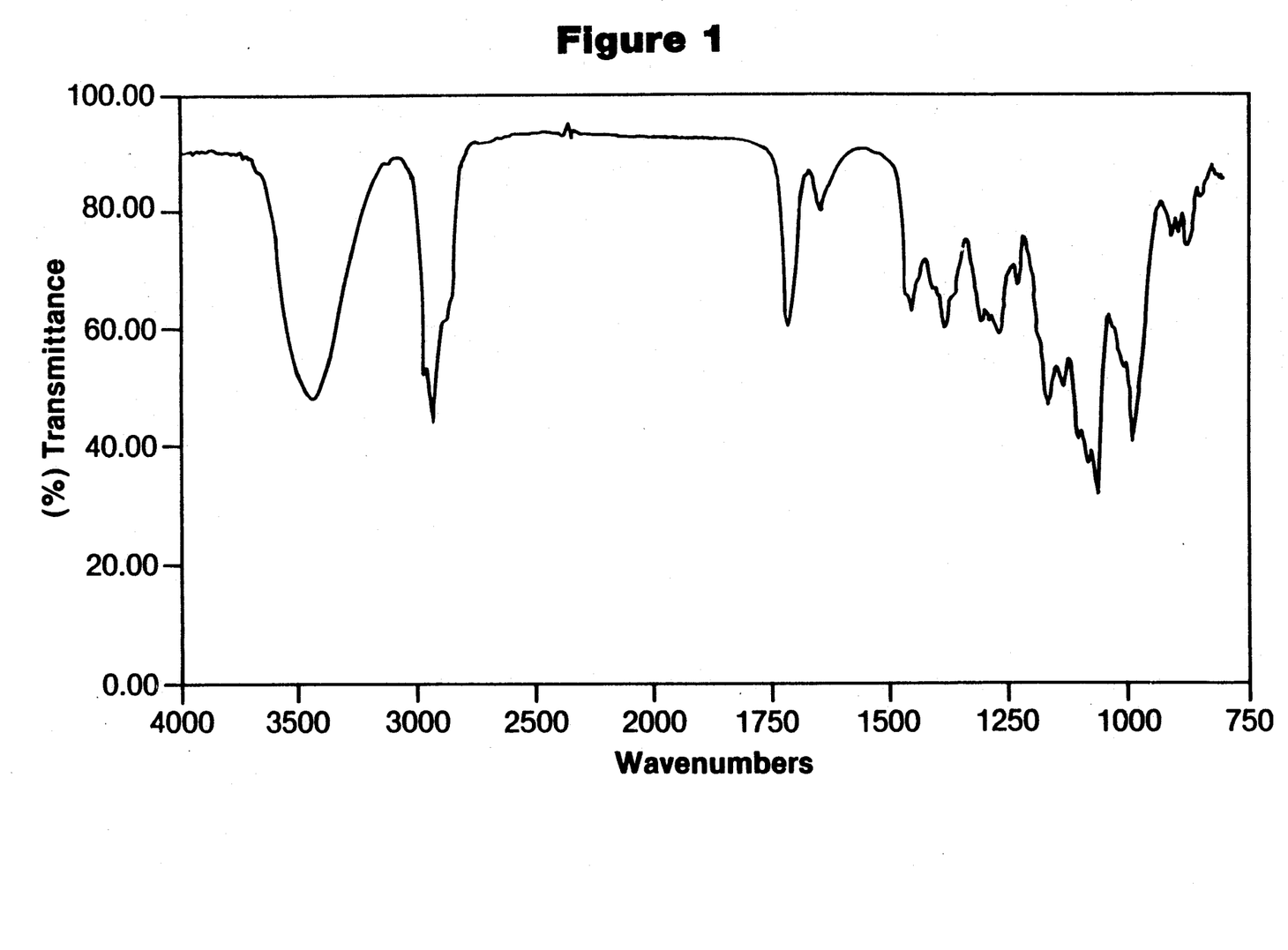
FIG. 1 -- A59770 factor A,
FIG. 2 -- A59770 factor A-aglycone,
FIG. 3 -- A59770 factor A-pentaacetyl derivative,
FIG. 4 -- A59770 factor B,
FIG. 5 -- A59770 factor C,
FIG. 6 -- A59770 factor D.

A59770A has the empirical formula $C_{53}H_{92}O_{17}$; the following optical rotations (c 1.0, $CHCl_3$, 25° C.): $-41°$ at $\lambda$ 589 nm and $-118°$ at $\lambda$ 365 nm; an ultraviolet spectrum having $\lambda_{max}$ at 211 nm (ethanol) and $\epsilon = 11{,}400$; an infrared spectrum having the following significant absorption maxima: 3453.8, 3449.0, 3436.4, 3426.8, 2934.9, 1166.1, 1101.4, 1085.0, 1064.8, and 987.6 $cm^{-1}$; a fast atom bombardment (FAB) mass spectrum $M+Na^+$ peak at 1023; and the following elemental analysis:

|   | Calculated % | Found % |
| --- | --- | --- |
| C | 63.57 | 63.36 |
| H | 9.26 | 8.96 |
| O | 27.17 | 27.19 |

A59770A aglycone

The aglycone of A59770A has the following structure

Figure 2:
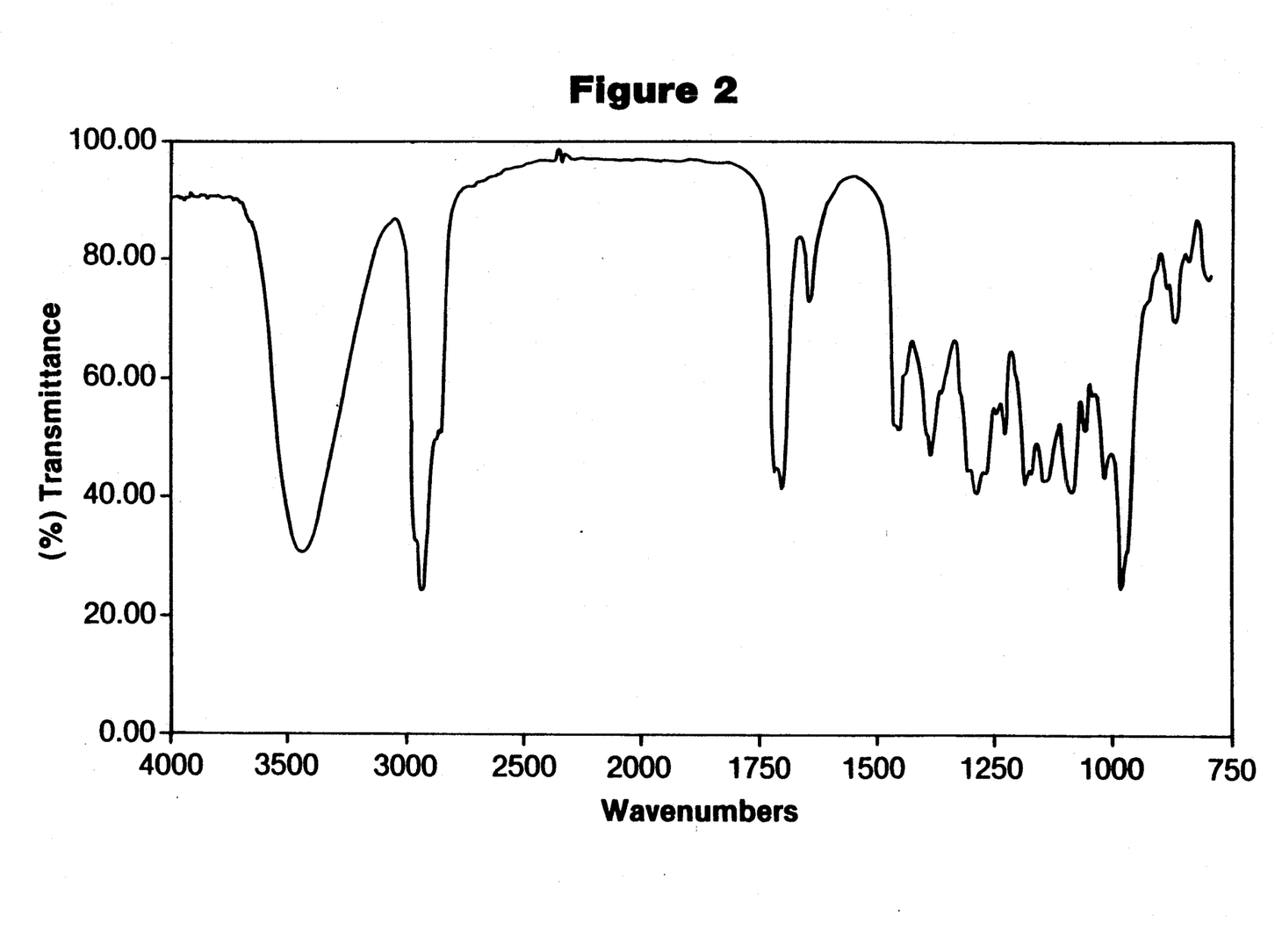

A59770A aglycone has the empirical formula $C_{40}H_{70}O_{11}$; the following optical rotations (c 1.0, CHCl$_3$, 25° C.): −38° C. at λ 589 nm and −99° at λ 365 nm; an ultraviolet spectrum having $\lambda_{max}$ at 214 nm (ethanol) and $\epsilon=10,000$; an infrared spectrum having the following significant absorption maxima: 3247.0, 3437.4, 2960.9, 2933.0, 1702.3, 1289.5, 1185.3, 1087.9, 1018.5 and 983.9 cm$^{-1}$; a FAB mass spectrum M+1 peak at 727; and the following elemental analysis:

|   | Calculated (%) | Found (%) |
|---|---|---|
| C | 66.10 | 66.15 |
| H | 9.71 | 9.90 |
| O | 24.19 | 24.13 |

Pentaacetyl-A59770A

Figure 3:
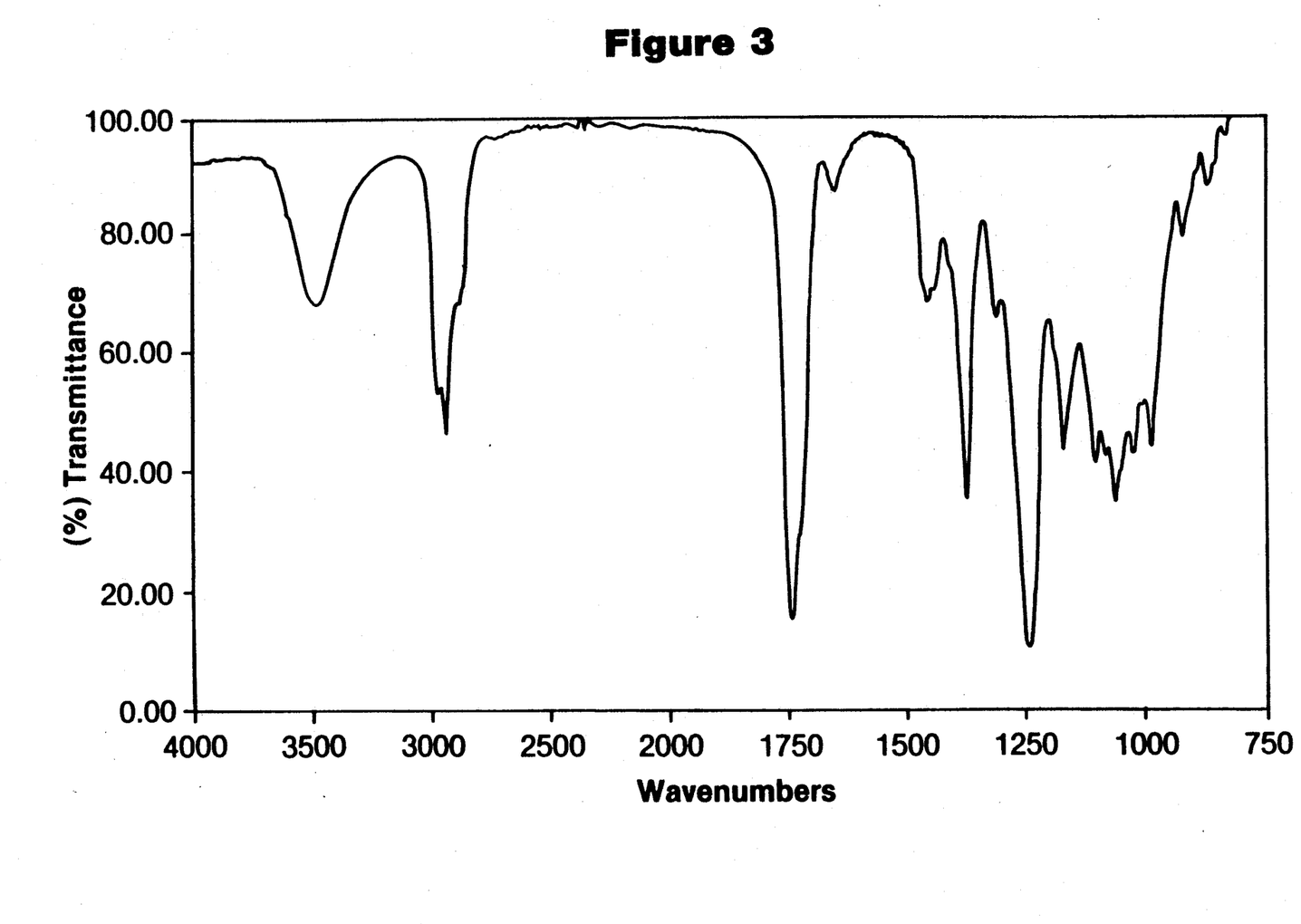

The pentaacetyl derivative of A59770A has the empirical formula $C_{63}H_{102}O_{22}$; the following optical rotations (c 1.0, CHCl$_3$, 25° C.): −23° at λ 589 nm and −72° at λ365 nm; an ultraviolet spectrum having a $\lambda_{max}$ (ethanol) at 211 nm and $\epsilon=13,200$; an infrared spectrum having the following characteristic absorption maxima: 2937.8, 1741.8, 1372.5, 1242.2, 1168.9, 1103.4, spectrum M+Na$^+$ peak at 1233; and the following elemental analysis:

|   | Calculated (%) | Found (%) |
|---|---|---|
| C | 62.46 | 62.70 |
| H | 8.49 | 8.19 |
| O | 29.05 | 28.99 |

A59770B

Figure 4:
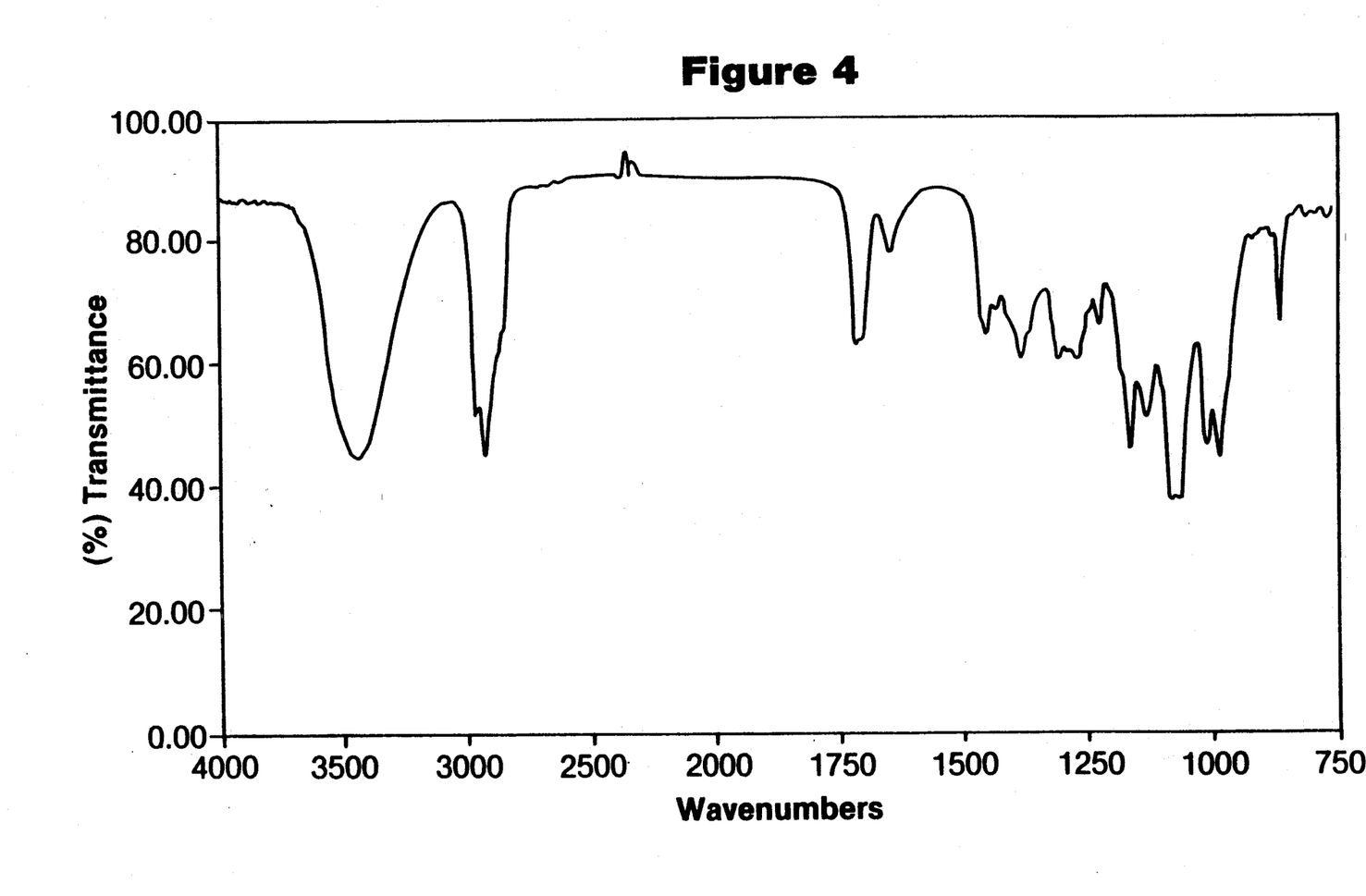

A59770B has the empirical formula $C_{52}H_{90}O_{17}$; the following optical rotations (c 0.99, CHCl$_3$, 25° C.): spectrum having a $\lambda_{max}$ (ethanol) at 213 nm and $\epsilon=11,300$; an infrared spectrum having the following significant absorption maxima: 3468.2, 3451.9, 3447.0, 3436.4, 3426.8, 2938.0, 1165.1, 1081.2, 1066.7 and 986.7 cm$^{-1}$; a FAB mass spectrum M+N peak at 1009; and the following elemental analysis:

|   | Calculated % | Found (%) |
|---|---|---|
| C | 63.26 | 62.99 |
| H | 9.19 | 9.39 |
| O | 27.55 | 27.34 |

A59770C

Figure 5:
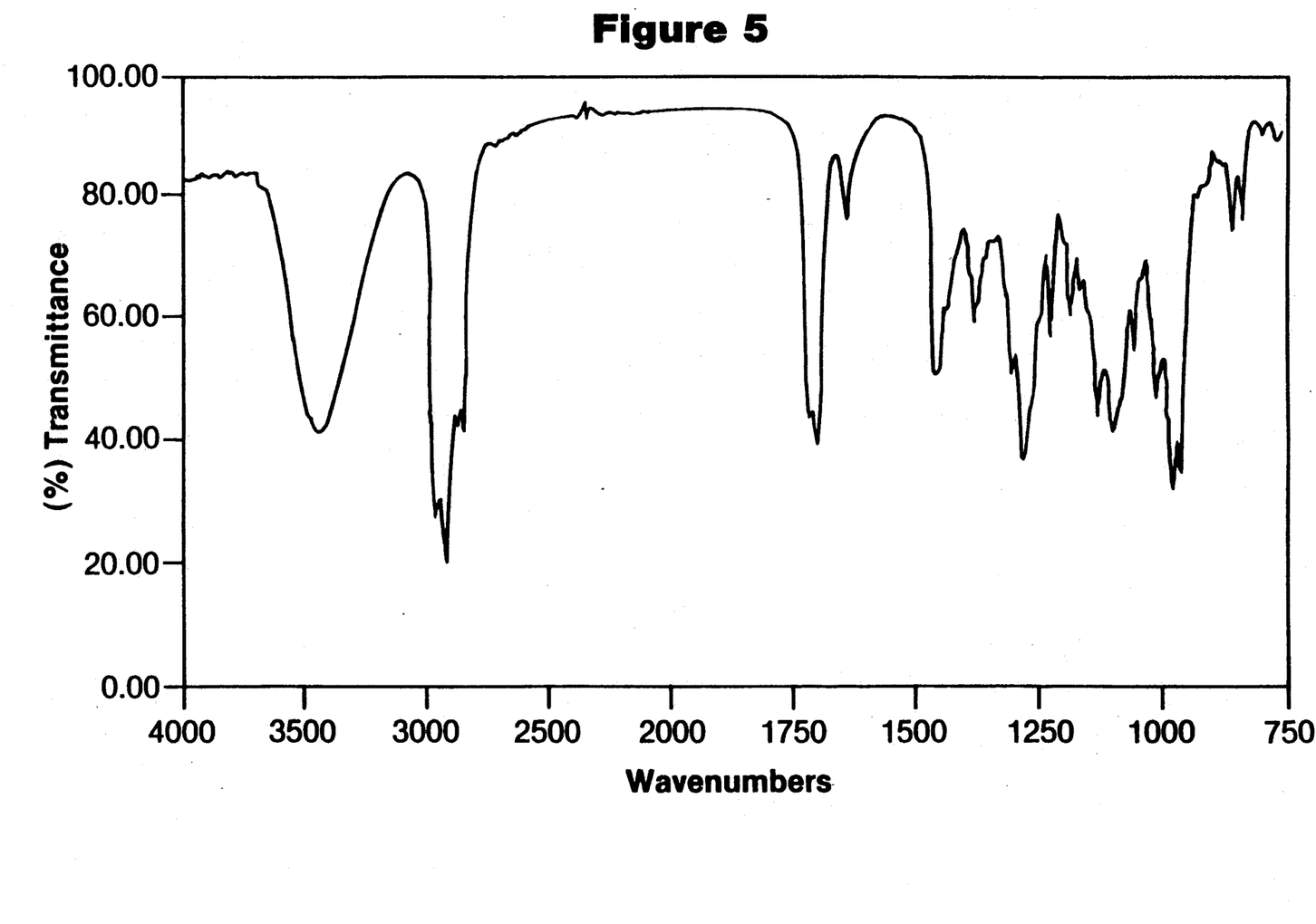

A5977C has the empirical formula $C_{40}H_{70}O_8$; the following optical rotations (c 1.0, CHCl$_3$, 25°): −30° at λ 589 nm and −75° at λ 365 nm; an ultraviolet spectrum having a $\lambda_{max}$ (ethanol) at 213 nm and $\epsilon=17,000$; an infrared spectrum having the following significant absorption maxima: 3446.1, 3434.5, 2866.7, 2824.9, 1701.3, 1281.8, 1103.36, 882.8, and 869.9 cm$^{-1}$; a FAB mass spectrum M+1 peak at 679; and the following elemental analysis:

|   | Calculated (%) | Found (%) |
|---|---|---|
| C | 70.76 | 70.50 |
| H | 10.39 | 10.26 |
| N | 18.85 | 18.58 |

A59770D

Figure 6:
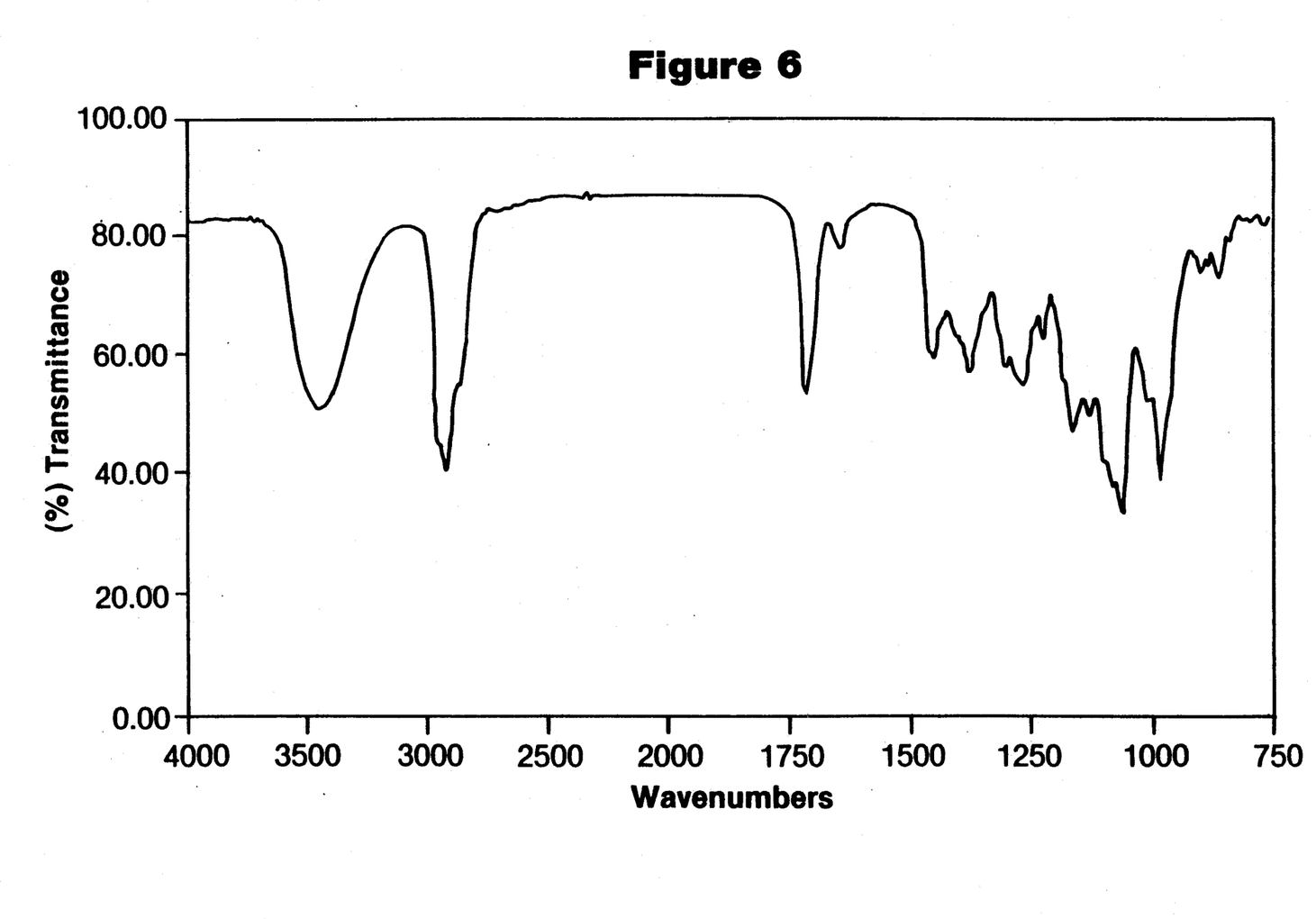

A59770D has the empirical formula $C_{54}H_{94}O_{17}$; the following optical rotations (C 0.99, CHCl$_3$, 25° C.): −42° at λ 589 nm and −118° at λ 365 nm; an ultraviolet spectrum having a $\lambda_{max}$ (ethanol) at 211 and $\epsilon=12,600$; an infrared spectrum having the following significant absorption maxima: 3452.8, 2961.9, 2858.1, 2834.9, 1166.1, 1132.3, 1102.4, 1084.1, 1065.7 and 987.6 cm$^{-1}$; a FAB mass spectrum M+NA$^+$ peak at 1037; and the following elemental analysis:

|   | Calculated (%) | Found (%) |
|---|---|---|
| C | 63.88 | 64.08 |
| H | 9.33 | 9.12 |
| N | 26.79 | 26.62 |

A59770E

A59770E has the empirical formula $C_{53}H_{92}O_{16}$ and a FAB mass spectrum M+N$^+$ peak at 1007.

A59770F

A59770F has the empirical formula $C_{53}H_{90}O_{17}$ and a FAB mass spectrum M+Na$^+$ peak at 1021.

The antibiotic complex is very toxic, thus making it useful as an agent to eliminate animals which threaten human life, such as, for example, rodents, rapid animals and the like. A59770A has been shown to have the following toxicity in mice:

| Mouse Acute Toxicity |
|---|
| LD$_{50}$ = 0.35 mg/kg i.p. |
| LD$_{50}$ = 0.88 mg/kg oral |

By comparison, strychnine has an MLD of 5 mg/kg orally in rats (*Merck Index*, p. 1268, 10th Ed. (Rahway, N.J., 1983).

Accordingly, proper laboratory safety procedures must be taken when producing or separating the complex or the individual factors.

The novel strain of this invention, *Amycolatopsis orientalis* NRRL 18387, was isolated from a soil collected from South Africa. The discussion below is a characterization and classification of *Amycolatopsis orientalis* NRRL 18387. This strain will be referred to herein as "culture A59770" or simply "A59770". This culture has been deposited and made a part of the stock culture collection of the Midwest Area Northern Regional Research Center, U.S. Department of Agriculture, Agricultural Research Service, Peoria, Ill. 61604, from which it is available to the public under the number NRRL 18387.

Data are presented to support the conclusion that A59770 is a strain of *Amycolatopsis orientalis* (Shinobu and Kawato) Pridham and Lyons 1970 (Pridham, T. G., 1970. "New Names and New Combinations in the Order Actinomycetales Buchanan 1917," *USDA Tech. Bull. No.* 424:32, Agricultural Research Service USDA, Washington, D.C.). This classification is based on simultaneous laboratory comparisons as well as examination of published descriptions of similar species.

Methods Used

The methods recommended by the International Streptomyces Project (ISP) for the characterization of Streptomyces species have been followed (Shirling, E. B. and D. Gottlieb, 1966, "Methods for Characterization of *Streptomyces* Species," *Int. J. Syst. Bacteriol.*, 16:313-340) along with certain supplementary tests (Blazevic, D. J. and G. M. Ederer, *Principles of Biochemical Tests in Diagnostic Microbiology*, John Wiley and Sons, Inc., New York, 1975, 136 p.).

Methods recommended for the characterization of *Nocardia* species by Gordon et al. [Gordon, R. E., D. A. Barnett, J. E. Handerhan, and C. H. Pang, 1974, "*Nocardia coeliaca, Nocardia autotrophica*, and the Nocardin Strain," *Int. J. Syst. Bacteriol.*, 24(1), 54-63] have been followed.

Resistance to rifampin and lysozyme was also that recommended by Gordon [Gordon, R. E. and D. A. Barnett, 1977, "Resistance to Rifampin and Lysozyme of Strains of Some Species of *Mycobacterium* and *Nocardia* as a Taxonomic Tool," *Int. J. Syst. Bacteriol.*, 27(3):176-178].

ISCC-NBS Centroid Color Charts, standard sample No. 2106 (Container Corporation of America, 1958), and the *Color Harmony Manual*, 4th ed., Container Corporation of America, Chicago, Illinois) were used to assign color names to the reverse side and to aerial spore mass, respectively.

Morphology was studied using an optical light microscope. A scanning electron microscope (SEM) was used to study the spore surface ornamentation.

Melanoid pigmet production (chromogenicity) was determined with ISP No. 1 (tryptone-yeast extract broth), ISP No. 6 (peptone-yeast extract iron agar), and ISP No. 7 (tyrosine agar).

The isomer of diaminopimelic acid (DAP) and the carbohydrates in hydrolysates of whole cells were established by the chromatographic methods of Becker et al. (Becker, B., M. P. Lechevalier, R. E. Gordon, and H. A. Lechevalier, 1964, "Rapid Differentiation between *Nocardia* and *Streptomyces* by Paper Chromatography of Whole-Cell Hydrolysates," *Appl. Microbiol.*, 12:421-423) and of Lechevalier (Lechevalier, M. P., 1968, "Identification of Aerobic Actinomycetes of Clinical Importance," *J. Lab. Clin. Med.*, 71:934-944), respectively.

Mycolic acids were determined by a method based on techniques described by Minnikin (Minnikin, D. E., I. G. Hutchinson and A. B. Caldicott, 1980, "Thin-layer Chromatography of Methanolysates of Mycolic Acid-containing Bacteria," *J. Chromatography*, 188:221-233).

NaCl tolerance was measured by adding NaCl to ISP No. 2 agar to equal the concentrations desired, and incubating the plates at 30° for 14 days.

Phosphatase and urease were determined by methods described by Blazevic et al. supra). Gelatin liquefaction was used for the determination of proteinase activity.

Resistance to antibiotics was measured by padding antibiotic sensitivity discs onto the surface of seeded ISP No. 2 agar plates.

Starch hydrolysis was determined by testing for the presence of starch with iodine on ISP No. 4 (inorganic salts-starch agar) plates (Blazevic et al. supra).

Hippurate hydrolysis was measured using Bacto Differentiation Disks for rapidly detecting the hydrolysis of hippurate.

Cultural Characteristics

Growth of A59770 was good on all complex and most defined media. Aerial mycelia had a spore mass color in the white color series. The nearest matching color tab in the Tresner and Backus system (Tresner, H. D. and E. J. Backus. 1956. System of Color Wheels for Streptomycete Taxonomy. *Appl. Microbiol.*, 11:335-338) was Oyxter White. The reverse side was generally a pale yellow, and occasionally a moderate brown depending on the medium. No soluble pigment was produced, except for a reddish-brown pigment on tyrosine agar (ISP No. 7). These cultural characteristics are presented in Table 1.

TABLE 1

Cultural Characteristics of A59770

| Agar Medium | Characteristics[a] | Agar Medium | Characteristics[a] |
|---|---|---|---|
| ISP No. 2 | G: Abundant - peels off surface | | G: Abundant |
| | R: 70.1.OY (peeled edges) | Calcium | R: 89.p.Yellow |
| | Am: Abundant, b Oyster White | Malate | Am: Good: b Oyster White |
| | Sp: None | | Sp: None |
| ISP No. 3 | G: Good | | G: Abundant |
| | R: 92.Y White | Glucose | R: 89.p.Yellow |
| | Am: Good: b Oyster White | Asparagine | Am: Abundant: a White |
| | Sp: None | | Sp: None |
| ISP No. 4 | G: Poor (almost no growth) | | G: Good |
| | R: 93.Y.Gray | Nutrient | R: 89.p.Yellow |
| | Am: Trace: b Oyster White | Agar | Am: Fair: b Oyster White |
| | Sp: None | | Sp: None |
| ISP No. 5 | G: Good | TPO[b] | G: Abundant |
| | R: 92.Y.White | | R: 87.m.Yellow |
| | Am: Fair: b Oyster White | | Am: Good: a White |
| | Sp: None | | Sp: None |
| Czapeks | G: Poor to Fair | TWA[c] | G: None |
| | R: 93.y.Gray | | R: None |
| | Am: Poor: b Oyster White (edges) | | Am: None |

TABLE 1-continued

Cultural Characteristics of A59770

| Agar Medium | Characteristics[a] | Agar Medium | Characteristics[a] |
|---|---|---|---|
| ISP No. 7 | Sp: None<br>G: Abundant (surface wrinkled)<br>R: 58.m.Br<br>Am: Abundant: d I.Gray to b White<br>Sp: Reddish-brown | YDA[d] | Sp: None<br>G: Fair (curled off surface of agar)<br>R: 89.p.Yellow<br>Am: Fair: a White (asporengeous)<br>Sp: None |

[a]G = growth R = reverse Am = aerial mycelia Sp = soluble pigment
[b]TPO = Tomato paste/oatmeal
[c]TWA = Tap water agar
[d]YDA = Yeast/dextrose agar

Morphological Characteristics

When A59770 was plated onto the surface of agar media such as yeast/malt extract agar (ISP No. 2), two morphological types of colonies were observed. The majority population is described infra. The minority type has the following characteristics: rare, occasional, clear, moist, mucoid, bald colonies with no aerial hyphae; irregular shape, edges curling forming ridges, center depressed; reverse color yellow-brown. When grown in pure culture, this mucoid isolate did not revert to the wild-type morphology. When recloned, the wild type did continue to produce the mucoid type. Both types produce the A59770 antibiotics.

Culture A59770 (majority population) produced an extensive substrate and a fairly well developed aerial mycelium. The aerial hyphae segment into long chains of conidia that have a cobweb appearance. This morphology is classified as characteristic of nonstreptomycetes in Bergey's Manual of Determinative Bacteriology (Buchanan, R. E., and N. E. Gibbons (eds.). 1974. Bergey's Manual of Determinative Bacteriology, 8th edition, The Williams and Wilkins Co., Baltimore).

The spore-surface ornamentation is smooth; spore shape is cylindrical; the spore size ranged from 1.3–1.8×0.3–0.5 µM, and averaged 1.5×0.4 µM.

When grown under submerged shaken conditions, the hyphae separated into fragments.

Physiological Characteristics

Culture A59770 produced acid from: arabinose, cellobiose, ethanol, fructose, galactose, glucose, glycerol, inositol, lactose, mannitol, mannose, melibiose, raffinose, rhamnose, salicin, trehalose, and xylose; utilized acetate, benzoate, citrate, lactate, malate, oxalate and succinate; decomposed casein, DNA, hypoxanthine and urea; hydrolyzed calcium malate and esculin.

Culture A59770 grew on Sabouraud dextrose agar, produced melanoid pigments on tyrosine agar only, liquefied gelatin, was able to grow at temperatures from 10°–37° C., and tolerated up to 6% NaCl.

Culture A59770 produced catalase, phosphatase, and urease; it was resistant to cephalothin, penicillin G, nalidixic acid, novobiocin, polymixin B, and trimethoprim.

The physiological properties of A59770 are summarized and compared with those of two related species, discussed infra, in Table 2.

TABLE 2

Comparison of Physiological Properties of A59770, N. aerocolonigenes and N. orientalis.[a]

| Property | A59770 | N. aerocolonigenes | N. orientalis |
|---|---|---|---|
| Acid Production From: | | | |
| Adonitol | − | − | + |
| L-Arabinose | + | + | + |
| D-Arabinose | + | ND | ND |
| Cellobiose | + | + | + |
| Cellulose | − | ND | − |
| Dextrin | − | ND | ND |
| Dulcitol | − | ND | − |
| Ethanol | + | ND | ND |
| i-Erythritol | − | − | + |
| D-Fructose | + | ND | + |
| D-Galactose | + | ND | + |
| Glucose | + | + | + |
| Glycerol | + | + | + |
| Glycogen | − | ND | ND |
| i-Inositol | + | + | + |
| Inulin | − | ND | + |
| D-Lactose | + | + | + |
| D-Maltose | − | + | + |
| D-Mannitol | + | + | + |
| D-Mannose | + | + | + |
| D-Melezitose | − | − | − |
| D-Melibiose | + | + | − |
| α-Me-D-Glucoside | − | − | + |
| D-Raffinose | + | − | − |
| L-Rhamnose | + | + | + |
| Salicin | + | ND | + |
| D-Sorbitol | − | − | − |
| Sucrose | − | ND | + |
| D-Trehalose | + | + | + |
| D-Xylose | + | + | + |
| Control | − | − | − |
| Hydrolysis of: | | | |
| Esculin | + | + | + |
| Hippurate | − | − | − |
| Starch | − | + | + |
| Growth-Sabouraud Dextrose | + | + | + |
| Nitrate Reduction | − | − | + |
| Survival at 50° C. for 8 hr. | − | − | + |
| Utilization of: | | | |
| Acetate | + | ND | + |
| Benzoate | + | − | − |
| Citrate | + | + | + |
| Lactate | + | ND | + |
| Malate | + | ND | + |
| Macate | − | − | − |
| Oxalate | + | ND | − |
| Succinate | + | + | + |
| Tartrate | − | − | − |
| Control | − | ND | − |
| Decomposition of: | | | |
| Adenine | − | − | − |
| Casein | + | + | + |
| DNA | + | ND | + |
| Hypoxanthine | + | + | + |
| Tyrosine | Tr. | + | + |
| Urea | + | + | + |
| Xanthine | Tr. | − | − |
| Calcium malate | + | + | + |
| Acid fastness | − | − | − |
| Gram stain | + | + | + |

TABLE 2-continued

Comparison of Physiological Properties of A59770, N. aerocolonigenes and N. orientalis.[a]

| Property | | A59770 | N. aerocolonigenes | N. orientalis |
|---|---|---|---|---|
| Elastin | | − | + | + |
| Testosterone | | Tr. | Tr. | + |
| NaCl tolerance: | | | | |
| 1% | | + | + | + |
| 2% | | + | + | + |
| 3% | | + | + | + |
| 4% | | + | + | + |
| 5% | | + | + | + |
| 6% | | + | − | + |
| 7% | | − | − | + |
| 8% | | − | − | + |
| 9% | | − | − | − |
| 10% | | − | − | − |
| Growth at (°C.): | | | | |
| 5 | | − | ND | − |
| 10 | | + | + | + |
| 15 | | + | ND | + |
| 20 | | + | ND | + |
| 25 | | + | ND | + |
| 30 | | + | ND | + |
| 37 | | + | ND | + |
| 40 | | − | ND | + |
| 42 | | − | ND | − |
| 45 | | − | − | − |
| 50 | | − | − | − |
| Resistance to: | Conc. | | | |
| Bacitracin | 10 units | − | − | − |
| Cephalothin | 30 mcg | + | + | + |
| Gentamicin | 10 mcg | − | − | − |
| Lincomycin | 2 mcg | − | + | + |
| Neomycin | 30 mcg | − | − | − |
| Oleandomycin | 15 mcg | − | − | − |
| Penicillin G | 10 units | + | + | + |
| Rifampin | 5 mcg | − | − | − |
| Streptomycin | 10 mcg | − | − | + |
| Tetracycline | 30 mcg | − | − | − |
| Tobramycin | 10 mcg | − | − | + |
| Vancomycin | 30 mcg | − | − | + |
| Chloramphenicol | 30 mcg | − | − | − |
| Erythromycin | 15 mcg | − | − | − |
| Nalidixic acid | 30 mcg | + | − | + |
| Novobiocin | 30 mcg | + | − | + |
| Polymixin B | 300 units | + | + | + |
| Trimethoprim | 5 mcg | + | + | + |
| Lysozyme | 50 μg/ml | − | + | − |
| Rifampin | 20 μg/ml | − | − | + |
| Melanoid pigment in: | | | | |
| ISP No. 1 broth | | − | ND | − |
| ISP No. 6 slants | | − | ND | − |
| ISP No. 7 slants | | + | ND | − |
| H₂S Production | | − | ND | ND |
| Catalase | | + | + | + |
| Urease | | + | + | + |
| Phosphatase | | + | + | + |
| Proteinase | | + | − | + |

[a] + = Uses or has trait
− = Doesn't use or doesn't have trait
ND = Not done
Tr = Trace

Cell Wall Analysis

Hydrolyzed whole cells contained the meso isomer of diaminopimelic acid. Sugars present in the whole cell hydrolysates were arabinose and galactose. The cell wall type, according to Becker et al., supra, is Type IV. The sugar pattern is Type A (Lechevalier, supra). Mycolic acids (LCN-A) were not produced. The cells stained Gram positive and were not acid-fast.

Identity of Strain A59770

The chemotaxonomic and general cultural characteristics are consistent with the assignment of strain A59770 to the genus Nocardia Trevisan 1889 (Skerman, V. B. D., V. McGowan, and P. H. A. Sneath (ed.), 1980, "Approved Lists of Bacterial Names," *Int. J. Syst. Bacteriol.*, 30:225–420).

Physiological properties of 14 species of Nocardia published by Gordon et al. (Gordon, R. E., S. K. Mishra and D. A. Barnett, 1978, "Some Bits and Pieces of the Genus Nocardia: *N. carnea, N. vaccinii, N. transvalensis, N. orientalis* and *N. aerocolonigenes*," *J Gen. Microbiol.*, 109:69-78) plus N. orientalis NRRL 2450 and *N. aerocolonigenes* NRRL 18049, were used to calculate similarity coefficients (Kurylowicz, W., A. Paszkiewicz, W. Woznicka, W. Kurzatkowski and T. Szulga, *Numerical Taxonomy of Streptomycetes*, Polish Medical Publishers, Warsaw, 1975, p. 37).

Two equations were used to calculate the coefficient of similarity. The coefficient of Jaccard ($S_J$) uses only positively similar ($N_S+$) and dissimilar ($N_d$) characters (Sneath, P. H. A., 1957, "The Application of Computers to Taxonomy," *J. Gen. Microbiol.*, 17:201):

$$S_J = \frac{N_s^+}{N_s^+ + N_d} \times 100$$

The simple matching coefficient (Sokal, R. R. and C. D. Michener, 1958, "A Statistical Method for Evaluating Systematic Relationships," *Kan. Univ. Sci. Bull.*, 38:1409) includes negatively similar characters:

$$S_{sm} = \frac{N_s^+ + N_s^-}{N_s^+ + N_s^- + N_d} \times 100$$

The results from these calculations are given in Table 3.

TABLE 3

Similarity Coefficients for A59770 and Other Nocardia Species.

| Culture | $S_{SM}$ | $S_J$ |
|---|---|---|
| A59770 | 100 | 100 |
| N. orientalis NRRL 18049 | 84 | 76 |
| N. aerocolonigenes | 84 | 75 |
| N. madurae | 71 | 56 |
| N. orientalis | 68 | 57 |
| N. amarae | 65 | 43 |
| N. orientalis NRRL 2450 | 63 | 53 |
| N. brasiliensis | 63 | 44 |
| N. hirsuta | 60 | 54 |
| N. autotrophica | 60 | 46 |
| N. vaccinii | 57 | 38 |
| N. caviae | 55 | 32 |
| N. dassonvillei | 51 | 33 |
| N. carnea | 50 | 24 |
| N. asteroides | 50 | 21 |
| N. pelletieri | 47 | 13 |
| N. transvalensis | 44 | 30 |

*Nocardia madurae* has been transferred from the genus Nocardia to the genus Actinomadura (Lechevalier and Lechevalier, gen. nov. 1970). Therefore, it was removed from consideration. Two species with high similarity coefficients are:

N. aerocolonigenes
N. orientalis

According to Goodfellow and Schaal (Goodfellow, M., and K. P. Schaal, "Identification Methods for Nocardia, Actinomadura and Rhodococcus," In F. A. Skinner and D. W. Lovelock (eds.), *Identification Methods for Microbiologists*, 2nd ed., Society for Applied Bacteriology Technical Series No. 14, Academic Press Inc., New York, 1979, p.261), neither of these species have mycolic acids, which indicates a close relationship to A59770.

Five additional strains given by Mordarska (Mordarska, H. and M. Mordarski, 1972, "Chemotaxonomic Characters and Classification of Some Nocardioform Bacteria," *J. Gen. Microbiology*, 71:77-86) which do not contain LCN-A, but which do have arabinose, are: *N. capreola, N. coeliaca, N. farcinica, N. rugosa,* and *N. tenuis*. Because the data which could be collected in the literature on these strains indicated they were less similar to A59770 than *N. aerocolonigenes* and *N. orientalis*, simultaneous laboratory comparisons were made with the latter two strains. Using 69 units of comparison for *N. aerocolonigenes* and 88 for *N. orientalis*, the following coefficients were calculated:

|                    | $S_{sm}$ | $S_j$ |
|--------------------|------|-----|
| A59770             | 100  | 100 |
| N. aerocolonigenes | 84   | 72  |
| N. orientalis      | 73   | 62  |

Three key properties given by Gordon et al., supra, to distinguish N. orientalis from N. aerocolonigenes are compared with those of A59770 in Table 4:

TABLE 4

Comparison of Key Properties of A59770, *N. aerocolonigenes* and *N. orientalis*

| Property | A59770 | N. aerocolon. | N. orientalis |
|---|---|---|---|
| Acid production from: | | | |
| erythritol | − | − | + |
| α-methyl-O-glucoside | − | − | + |
| Lysozyme resistance | − | + | − |

Inspection of these indicators shows that A59770 is most similar to *N. Aerocolonigenes*.

Using the key devised by Mishra [Mishra, S. J., Gordon, R. E., and D. A. Barnett, 1980, "Identification of Nocardiae and Streptomyces of Medical Importance," *J. Clin. Microbiol.*, 11(6):728-736], culture A59770 keyed directly to *N. aerocolonigenes*.

Cultural comparisons showed *N. aerocolonigenes* had no aerial hyphae, while A59770 produced abundant white aerial mycelia. This characteristic represents the main difference between these two strains. Development of aerial hyphae is a variable property among the Nocardia, and in *N. aerocolonigenes* particularly (Mishra, et al., *supra*). The original description of *N. aerocolonigenes* (Shinobu, Ryuji and Kawato, 1960, "On *Streptomyces aerocolonigenes* nov. sp., Forming the Secondary Colonies on the Aerial Mycelia," *Bot. Mag. Tokyo*, 73:213-216) stated that aerial mycelia were present, but there was a tendency to lose this ability. When formed, the aerial mycelia were white. Therefore, this cultural difference was not given undue significance.

The similarity coefficient of 84 with the type species and with the NRRL 18049 strain is considered sufficient evidence to classify A59770 as a strain of *Nocardia aerocolonigenes* (Shinobu and Kawato) Pridham and Lyons 1970. Although *N. aerocolonigenes* is not in the *Approved Lists of Bacterial Names* (Skerman, et al., supra), and consequently is not a validly published species, it is recognized extensively in the literature.

However, recently, the new genus Saccharothrix (Labeda, D. P., R. T. Testa, M. P. Lechevalier, and H. A. Lechevalier, 1984, "Saccharothrix: a New Genus of the Actinomycetales Related to Nocardiopsis," *Int. J. Syst. Bacteriol.,* 34:426-431) was established, *Nocardia aerocolonigenes* was transferred into this genus [Labeda, D. P., 1986, "Transfer of *Nocardia aerocolonigenes* (Shinobu and Kawato 1960) Pridham 1970 into the genus Saccharothrix Labeda, Testa, Lechevalier and Lechevalier 1984 as *Saccharothrix aerocolonigenes* sp. nov.," *Int. J. Syst. Bacteriol.,* 36:109-110]. This transfer leads to the conclusion that culture A59770 should be classified as *Amycolatopsis orientalis.*

This conclusion is reached because Saccharothrix has a different chemotaxonomy than Nocardia. The main difference is the cell-wall type. Saccharothrix has a type III cell wall (meso-DAP, galactose and rhamnose present as characteristic whole cell sugars). Nocardia has a type IV cell wall (meso-DAP, galactose and arabinose present). The absence of arabinose in *Saccharothrix* is diagnostic.

Nocardia aerocolonigenes was transfered into the genus Saccharothrix on the basis of its cell wall chemistry after the taxonomic studies of A59770 were completed. Because it has a type IV cell wall, however, A59770 does not belong in the genus Saccharothrix.

More recently, the new genus Amycolatopsis (Lechevalier, M. P., H. Prauser, D. P. Labeda, and J.-S. Ruan, "Two New Genera of Nocardioform Actinomycetes: Amycolata gen. nov. and Amycolatopsis gen. nov.," *Int. J. Syst. Bacteriol.,* 36:29-37) was established to accomodate *N. orientalis* cultures. Culture A59770 fits into this new genus.

A phospholipid analysis of A59770 indicated the presence of phosphatidylethanolamine, which is diagnostic for a type PII. This characteristic suggests that A59770 should be placed into the genus Amycolatopsis. In addition, the initial descriptions of A59770 indicated a close similarity to *N. orientalis.* Therefore, culture A59770 is classified as a strain of *Amycolatopsis orientalis* (Pittenger and Brigham 1956) comb. nov.

The A59770 complex, individual A59770 factors A, B, C, D, E and F and the aglycone and pentaacetyl derivative of A59770 factor A (A59770 compounds) are very toxic to rodents and thus are useful as rodenticides. Rodenticides are usually presented to rats or mice in the form of mixtures with foodstuffs. The concentration of rodenticide in the mixture is adjusted so that the rodents consume an amount of the rodenticide which is either acutely or chronically lethal. It is advisable not to make the mixture so concentrated that the rodent dies immediately, or even soon after eating. Rodents, and especially rats, are intelligent enough to understand the causal relationship between feeding and death if the time interval is very short. Thus, the best practice is to adjust the concentration of the rodenticide so that the rodents will be poisoned over a number of feedings at the poison bait.

In special circumstances, rodenticides are sometimes mixed in drinking water, or prepared as "tracking powders" which are deposited in runways used by the rodents. After the animals have walked through the loose poison powder, they lick their feet clean and thus ingest the rodenticide.

Thus, this invention provides a method of reducing a population of rodents, such as rats or mice, which comprises supplying to a locus frequented by the rodent a rodenticidally-effective amount of an A59770 compound. The invention also provides rodenticidal compositions which comprise inert carriers and an effective rodenticidal concentration of an A59770 compound and a carrier therefor.

The compounds of the present invention also possess some antimicrobial activity.

EXAMPLE 1

Preparation of Antibiotic A59770

A. Shake-Flask Fermentation

The culture, *Amycolatopsis orientalis comb. nov.* NRRL 18387, either as a lyophilized pellet or as a suspension which had been maintained in the vapor phase under liquid nitrogen, is used to inoculate a seed medium with the following composition:

| SEED MEDIUM | |
| --- | --- |
| Ingredient | Amount (%) |
| Glucose | 1.0 |
| Potato dextrin | 2.0 |
| Yeast extract | 0.5 |
| NZ Amine* | 0.5 |
| CaCO$_3$ | 0.1 |
| Deionized water | q.s. 100% |

*NZ Amine; Sheffield Chemical Co., Norwich, NY

The pH of the medium is adjusted to to 7.0 with 5N NaOH prior to autoclaving.

Slants or plates are prepared by adding 1.5% agar to the seed medium.

The inoculated medium is incubated at 30° C. for 10–14 days. The mature culture is scraped with a sterile tool to loosen the spores, remove and macerate the mycelial mat. These cells are used to prepare vials of lyophilized cells or to grow the microorganism in the seed medium for storage under the vapor phase of liquid nitrogen.

The sterile seed medium (50 mL in a 250 mL wide-mouth Erlenmeyer flask) is inoculated with 2 mL of cells which have been maintained under the vapor phase of liquid nitrogen. The inoculated first stage medium is incubated at 30° C. for 48 hours on a rotary shaker orbiting in a two-inch (5.08 cm) circle at 250 rpm.

This inoculated first-stage medium (1.0 mL) is used to inoculate 50 mL of a production medium having the following composition:

| Ingredient | Amount (%) |
| --- | --- |
| Cotton seed flour* | 0.5 |
| Cotton seed oil** | 0.5 |
| Casein | 0.1 |
| CaCO$_3$ | 0.25 |
| Blackstrap molasses | 0.3 |
| Glucose | 2.0 |
| Deionized water | q.s. 100% |

*Proflo, Traders Protein, Memphis, TN.
**Proflo Oil, Traders Protein, Memphis, TN.

The pH of the medium is adjusted to to 7.0 with 5N NaOH prior to autoclaving.

The inoculated fermentation medium is incubated in 250-mL wide-mouth Erlenmeyer flasks at 30° C. for 5 days on a rotary shaker orbiting in a two-inch circle at 250 rpm.

B. Stirred Bioreactor Fermentation (100 Liters)

In order o provide a larger volume of inoculum, 10 mL of incubated first-stage medium, as described in section A, is used to inoculate 400 mL of a second stage growth medium having the same composition as that of the first-stage medium. This second-stage vegetative medium is incubated in a two liter wide-mouth Erlenmeyer flask for 48 hours at 30° C. on a rotary shaker orbiting in a two-inch circle at 250 rpm.

Incubated second-stage vegetative medium (800 mL) thus prepared is used to inoculate 100 liters of sterile production medium, prepared as described in section A. The inoculated medium is allowed to ferment in a 165-liter stirred bioreactor for 120 hours at 30° C. The pH of the fermentation medium is maintained at 7.0 by adding 5N NaOH as needed. Moderate airflow (25 CFM) and low rpm (80) in the bioreactor are used to maintain the dissolved oxygen level at 65% of air saturation.

C. Stirred Bioreactor Fermentation (1200 Gallons)

In order to generate even more material, the fermentation is carried out at described in Sections A and B, but adapting the process to a 1600-gallon stirred bioreactor containing 1200 gallons of production medium. A large quantity of the second-stage medium (2.5 liters) is used to inoculate 120 liters of seed medium in a 165-liter stirred bioreactor. The cells are grown for 48 hours at 30° C. while being agitated at 80 rpm with an air flow of 25 cubic ft/min (CFM).

The inoculated seed medium (100 liters) is used to inoculate 1200 gallons of production medium having the composition described in Section A.

The inoculated medium is allowed to ferment in a 1600 gallon stirred bioreactor for about 120 hours at 30° C. The pH of the fermentation medium is maintained at 7.0 by adding 5N NaOH as required. An air flow of 25 CMF and slow agitation at 80 rpm in the stirred vessel maintains the dissolved oxygen level at approximately 70% of air saturation. The fermentation is harvested after approximately 120 hours incubation.

EXAMPLE 2

Isolation of A59770 Complex

Whole fermentation broth (4100 L) was filtered using filter aid (Hyflo-Super-Cel). The mycelial cake was then extracted twice with methanol (400 L each time) in a press. The extracts were combined and concentrated under vacuum to approximately 300 L. The concentrate was then combined with 100 L of Diaion HP-20 resin (Mitsubishi Chem. Ind., Ltd., Tokyl, Japan) suspended in 1200 L of water. The mixture was agitated for 2 hours and then transferred into a column. The column effluent was discarded and the resin washed with 250 L of water and 250 L of methanol: water (1:1). Both solutions were discarded. The resin was then eluted with methanol at a rate of about 3 L/min, and multiple 25-L fractions were collected. Each fraction was analyzed using an analytical HPLC system. Fractions containing the active factors A59770A, B, C, D, E, or F were combined, concentrated to an oily residue, and rinsed with n-hexane to remove inactive lipids and lipid-like materials. The remaining residue was then treated with toluene to dissolve the crude active complex.

EXAMPLE 3

Purification of A59770 Complex

The concentrated toluene extract (0.8 L) was purified by chromatography using a Waters Prep-500 and Waters silica gel cartridges (Waters Assoc., Milford, Mass., 01757). Five different runs were made, using two cartridges in tandem each time. For each chromatographic run, 160 mL of the extract were loaded onto the top cartridge, and the elution was carried out using a linear gradient, starting from 4 L of toluene and going to 4 L of ethyl acetate, followed by 4 L of ethyl acetate, collecting 250-mL fractions. Each fraction was analyzed for the active complex using analytical HPLC. Similar fractions containing the active complex, or portions of it, from each of the five runs were combined, concentrated and lyophilized to give the following preparations:

| No. | Amount | Content |
| --- | --- | --- |
| 1 | 101.6 g | 80% factor A |
| 2 | 14.0 g | 45% factor A |
| 3 | 21.8 g | 74% factor B |
| 4 | 8.0 g | minor factors |
| 5 | 8.8 g | 74% factor C |
| 6 | 1.0 L | unknown materials |

EXAMPLE 4

Purification of A59770A

A 1.0-g portion of A-enriched complex, prepared as described for Preparation 1 in Example 3, was dissolved in 5 mL of methanol and applied to a 4.7×45 cm Michel-Miller high-performance-low-pressure liquid chromatography (HPLPLC) glass column (Ace Glass, Inc., Vineland, N.J. 08360) packed with 10-20 micron LP-1/C-18 reversed-phase silica gel. The reversed-phase silica gel was prepared as described in Examples 6 and 7 of U.S. Pat. No. 4,299,763 (Nov. 10, 1981). An FMI valveless piston pump (Fluid Metering Inc., Oyster Bay, N.Y. 11771) was used to elute the column at 12 ml/min (100 psi). The column was initially conditioned with methanol:acetonitrile:water (Solvent A) at a ratio of (30:30:40). The column was then developed using a linear gradient of 2 L of solvent A at that ratio and 2 L of solvent A at the ratio (45:45:10), followed by 1 L of solvent A at the latter ratio, collecting 25-mL fractions.

The eluate was monitored by UV at 254 nm, using an ISCO Model UA-5 monitor. Fractions of interest were analyzed using analytical HPLC. Fractions with similar profiles were combined, concentrated and lyophilized to give the following preparations:

| No. | Fractions | Wt (mg) | Factors |
| --- | --- | --- | --- |
| 1 | 71–73 | 10 | B |
| 2 | 74–77 | 42 | A, B |
| 3 | 78–83 | 376 | A |
| 4 | 84–94 | 332 | A |
| 5 | 98–100 | 19 | D |
| 6 | 101–105 | 111 | D, E, F |
| 7 | 106–110 | 38 | E, F |

EXAMPLE 5

Purification of A59770B

A 2.0-g portion of Preparation 3 from Example 4 was dissolved in 5 mL of methanol and applied to a glass column as described in Example 4. The column was conditioned and developed with solvent A, conditioning with the ratio (30:30:40) and then developing using a linear gradient of 2 L of (30:30:40) and 2 L of (42.5:42.5:15), followed by a linear gradient of 0.5 L of (42.5:42.5:15) and 0.5 L of (45:45:10), collecting 25-mL fractions. The eluate was monitored as described in Example 4. Fractions containing A59770B (353 mg) were combined with similarly prepared fractions from two other runs concentrated and lyophilized to give 946 mg of A59770B.

EXAMPLE 6

Purification of A59770C

A 1.0-g portion of Preparation 5 from Example 4 was dissolved in 5 mL of methanol and applied to a 4.7×45 cm glass column as described in Example 4. The column was conditioned and developed in solvent A, conditioning at the ratio (35:35:30) and then developing using a linear gradient of 2 L of (45:45:10). Fractions were analyzed by analytical HPLC. Fractions containing A59770C were pooled, concentrated and lyophilized to give 273 mg of A59770C.

EXAMPLE 7

Purification of A59770D

A 1.0-g portion of A59770 complex similar to that described in Example 1 was dissolved in 5 mL of methanol and applied to a 4.7 x 45 cm glass column as described in Example 4. The column was conditioned and developed in solvent A, conditioning at the ratio (30:30:40) and then developing using a linear gradient of 2 L of (30:30:40) and 2 L of (45:45:10). Fractions were analyzed by analytical HPLC. Fractions containing A59770D were combined, concentrated and lyophilized to give 19 mg of A59770D.

EXAMPLE 8

Purification of A59770E

A 100-mg portion of A59770 complex containing A59770 factors E and F, prepared in a similar way as preparations 6 and 7 in Example 4, was dissolved in 2 mL of methanol and applied to a 2.5×30 cm Michel-Miller column (Ace Glass, Inc., Vineland, N.J. 08360) packed in our laboratories with 15–25 micron LiChroprep RP-18 [hydrocarbon phase (C18) chemically bonded to silica gel, from MC/B Manufacturing Chemists, Inc., Cincinnati, Ohio]. The other instruments used were the same as those described in Example 4. The column was conditioned and developed in solvent A, conditioning at the ratio (35:35:30) and then developing using a linear gradient of 2 L of A at (35:35:30) and (45:45:10). Fractions were analyzed by analytical HPLC. The fraction containing A49770E was concentrated and lyophilized to give 5 mg of A59770E.

EXAMPLE 9

Separation of A59770F

Preparation 7 from Example 4, containing a mixture of A59770E and A59770F was separated and analyzed by analytical HPLC and FAB/MS. A59770E had an HPLC retention time (R.T.) of 11:67 minutes, and A59770F had an R.T. of 12:87 minutes. Peak matching established that the slower eluting compound (R. T. 12:87 minutes) had an empirical formula of $C_{53}H_{90}O_{17}$.Na (MW 1021), thus differentiating this factor from A59770E.

EXAMPLE 10

Pentaacetyl Derivative of A59770A

A59770A (250 mg) was allowed to stand in pyridine (5 mL) and acetic anhydride (5 mL) for 5 days at room temperature. The solution was concentrated, dissolved in acetone (5 mL) and concentrated again. Concentration with acetone was repeated until all pyridine was removed.

EXAMPLE 11

A59770 Factor A Aglycone

A59770A (11 g) in 1 L of methanol:0.1N HCl (9:1) was stirred for 8 hr, then left at room temperature overnight. HPLC showed that 80% of the material was hydrolyzed. After being stirred for an additional 8 hr, 95% was converted to the aglycone. Water was added, and the aglycone was extracted with chloroform. The product was purified by preparative HPLC to yield 7.0 grams of the pure algycone.

We claim:

1. Antibiotic A59770 Factor A, which has the structure

2. Antibiotic A59770 factor A aglycone, which has the following structure:

3. Antibiotic A59770 factor C, which has the following characteristics:
   (a) an empirical formula of $C_{40}H_{70}O_8$;
   (b) an optical rotation (c 1.0, CHCl$_3$, 25° C. of $-30°$ C. at $\lambda=589$ nm and $-75°$ at $\lambda=365$ nm;
   (c) an ultraviolet spectrum having a $\lambda_{max}$ (ethanol) at 213 nm and $\epsilon=17,000$;
   (d) A FAB mass spectrum having an M+1 peak at 679; and
   (e) an infrared spectrum as shown in FIG. 5.

4. Antibiotic A59770 factor D, which has the following characteristics:
   (a) an empirical formula of $C_{54}H_{94}O_{17}$;
   (b) an optical rotation (c 0.99, CHCl$_3$, 25° C.) of $-42°$ at $\lambda=589$ nm and $-118°$ at $\lambda=365$ nm;
   (c) an ultraviolet spectrum having a $\lambda_{max}$ (ethanol) at 211 and $\epsilon=12,600$;
   (d) a FAB mass spectrum having an M+N$^+$ peak at 1037; and
   (e) an infrared spectrum as shown in FIG. 6.

5. The pentaacetyl derivative of A59770 factor A, which has the following characteristics:
   (a) an empirical formula of $C_{63}H_{102}O_{22}$;
   (b) the following optical rotations (c 1.0, CHCl$_3$, 25° C.): $-23°$ at $\lambda$ 589 nm and $-72°$ at $\lambda$ 365 nm;
   (c) an ultraviolet spectrum having $\lambda$max (ethanol) at 211 nm and $\epsilon=13,200$;
   (d) a FAB mass spectrum M+Na$^+$ peak at 1233; and
   (e) an infrared spectrum as shown in FIG. 3.

* * * * *

UNITED STATES PATENT AND TRADEMARK OFFICE
CERTIFICATE OF CORRECTION

PATENT NO. : 5,239,064
DATED : August 24, 1993
INVENTOR(S) : Marbin Hoehn, et al.

Page 1 of 2

It is certified that error appears in the above-indentified patent and that said Letters Patent is hereby corrected as shown below:

Column 18, lines 1-18,

UNITED STATES PATENT AND TRADEMARK OFFICE
CERTIFICATE OF CORRECTION

PATENT NO. : 5,239,064          Page 2 of 2
DATED     : August 24, 1993
INVENTOR(S) : Marvin Hoehn, et al.

It is certified that error appears in the above-indentified patent and that said Letters Patent is hereby corrected as shown below:

should read --  --.

Signed and Sealed this

Tenth Day of October, 1995

Attest:

BRUCE LEHMAN

Attesting Officer       Commissioner of Patents and Trademarks